United States Patent [19]

Berger et al.

[11] 4,234,487

[45] Nov. 18, 1980

[54] PROCESS OF MAKING A CARBAZOLE ACETIC ACID

[75] Inventors: Leo Berger, Montclair; John W. Scott, Upper Montclair, both of N.J.

[73] Assignee: Hoffmann-La Roche Inc., Nutley, N.J.

[21] Appl. No.: 35,669

[22] Filed: May 3, 1979

Related U.S. Application Data

[62] Division of Ser. No. 972,142, Dec. 21, 1978, Pat. No. 4,179,443, which is a division of Ser. No. 914,465, Jun. 12, 1978, Pat. No. 4,146,542.

[51] Int. Cl.$^3$ .............................................. C07D 209/82
[52] U.S. Cl. ..................................................... 260/315
[58] Field of Search ........................................ 260/315

[56] References Cited

PUBLICATIONS

Buehler et al., "Survey of Organic Chemistry", (1970), Wiley–Interscience, p. 143.

Sumpter, "Heterocyclic Compounds with Indole and Carbazole Systems," (1954), pp. 73 and 74.

*Primary Examiner*—Henry R. Jiles
*Assistant Examiner*—R. W. Ramsuer
*Attorney, Agent, or Firm*—Jon S. Saxe; George M. Gould; William G. Isgro

[57] ABSTRACT

A process for preparing 6-chloro-α-methylcarbazole-2-acetic acid and esters thereof by the steps of:

(a) reacting 6-chloro-1,2,3,4-tetrahydrocarbazole-2-one with a trialkyl-α-methylphosphonoacetate to yield corresponding 3,4-dihydro-α-methylcarbazole-2-acetic acid ester; and (b) aromatizing the reaction product of step (a), prior to or after saponification, to yield, respectively, 6-chloro-α-methylcarbazole-2-acetic acid or ester, is described. Additionally, there are described 6-chloro-1,2,3,4-tetrahydrocarbazole-2-one useful as an intermediate, and dihydrocarbazoles useful as intermediates and/or as anti-inflammatory and antirheumatic agents.

1 Claim, No Drawings

PROCESS OF MAKING A CARBAZOLE ACETIC ACID

This is a division of application Ser. No. 972,142, filed Dec. 21, 1978 now U.S. Pat. No. 4,179,443, which in turn is a divisional application of U.S. Patent Application Ser. No. 914,465, filed June 12, 1978 now U.S. Pat. No. 4,146,542.

BRIEF SUMMARY OF THE INVENTION

The invention relates to a process for the preparation of 6-chloro-α-methylcarbazole-2-acetic acid and esters thereof which comprises:
(a) treating 6-chloro-1,2,3,4-tetrahydrocarbazole-2-one with a trialkyl-α-methylphosphonoacetate in the presence of a strong base; and
(b) prior to or after saponification of the resulting 6-chloro-3,4-dihydrocarbazole-α-methyl-2-acetic acid ester, aromatizing said 6-chloro-3,4-dihydrocarbazole-α-methyl-2-acetic acid or ester to yield 6-chloro-α-methylcarbazole-2-acetic acid or ester, respectively.

In another aspect, the invention relates to 6-chloro-1,2,3,4-tetrahydrocarbazole-2-one, a compound characterized by the structural formula

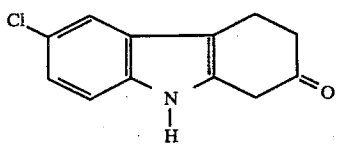

I

In yet another aspect, the invention relates to compounds of the formula

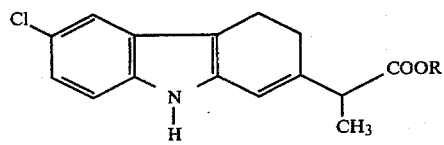

V wherein R is hydrogen or lower alkyl, or, when R is hydrogen, a salt thereof with a pharmaceutically acceptable base, and 6-chloro-3,4-dihydro-2-(2-hydroxymethylethyl)carbazole, characterized by the structural formula

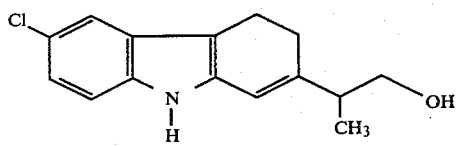

VI

DETAILED DESCRIPTION OF THE INVENTION

The invention relates to a process for preparing 6-chloro-α-methylcarbazole-2-acetic acid and esters thereof which comprises:
(a) reacting 6-chloro-1,2,3,4-tetrahydrocarbazole-2-one with a trialkyl-α-methylphosphonoacetate in the presence of a strong base; and
(b) aromatizing the resulting 6-chloro-3,4-dihydro-α-methylcarbazole-2-acetic acid ester, that is, the reaction product of step (a), either prior to or after saponification, to yield 6-chloro-α-methylcarbazole-2-acetic acid or ester thereof.

More specifically, the process comprises reacting 6-chloro-1,2,3,4-tetrahydrocarbazole-2-one of the formula

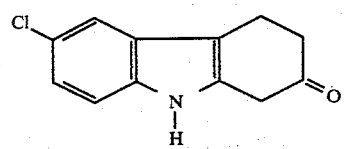

I with a trialkyl-α-methylphosphonoacetate of the formula

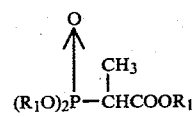

IV wherein $R_1$ is lower alkyl, in the presence of a strong base, to yield a compound of the formula

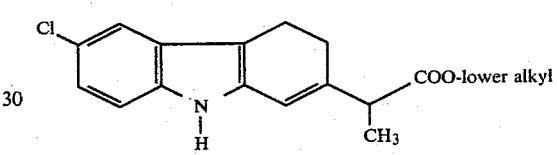

Va which, if desired, can be saponified with acid or base, to the corresponding acid; and, thereafter, aromatizing the compound of the formula

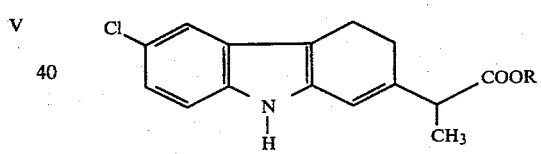

V wherein R is hydrogen or lower alkyl, to yield the corresponding compound of the formula

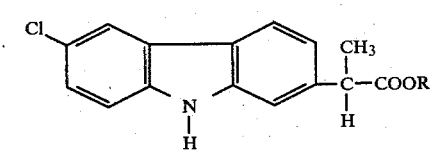

II wherein R is hydrogen or lower alkyl.

Exemplary of the compounds of formula V are:
6-chloro-3,4-dihydrocarbazole-2-α-methylacetic acid;
6-chloro-3,4-dihydrocarbazole-2-α-methylacetic acid ethyl ester;
6-chloro-3,4-dihydrocarbazole-2-α-methylacetic acid methyl ester; or the like.

The reaction of the 6-chloro-1,2,3,4-tetrahydrocarbazole-2-one of formula I with tri-lower alkyl-α-methylphosphonoacetate, for example, with triethyl-α-methylphosphonoacetate, can be carried out in an inert organic solvent, for example, a hydrocarbon such as benzene, tetrahydrofuran, dimethylsulfoxide, or the like. This reaction can be effected at or above room temperature, for example, at a temperature in the range of from about 25° C. to about 100° C., preferably in the range of from about 25° C. to about 50° C. The reaction is carried out in the presence of a strong base, for example, sodium hydride, or the like. The resulting 3,4-dihydrocarbazole-α-methyl-2-acetic acid ester, that is, a compound of formula Va, can be recovered by conventional methods or can be reacted in situ in the next step of the process, that is, in the aromatization step.

The aromatization of the 3,4-dihydrocarbazole-α-methyl-2-acetic acid or ester of formula V to the corresponding carbazole compound of formula I, can be carried out, for example, with p-chloranil, o-chloranil, 2,3-dichloro-5,6-dicyanobenzoquinone (DDQ), sulfur, lead oxide, or the like, in the presence of an inert organic solvent, for example, xylene, benzene, toluene, quinoline, dimethylsulfoxide, dimethylformamide, or the like. The aromatization is conducted, preferably at the reflux temperature of the reaction mixture. The formed product, i.e., a compound of formula I, can be recovered in accordance with known procedures, for example, by recrystallization or the like.

A 3,4-dihydrocarbazole compound of the formula

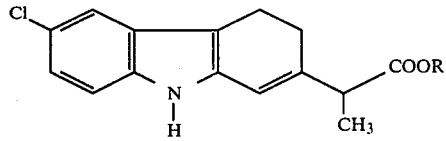

V where R is as previously described, can be converted to the corresponding alcohol of the formula

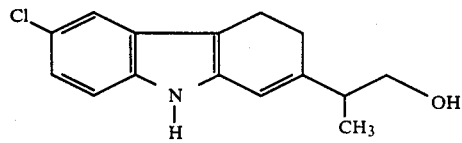

VI

More specifically, a compound of formula V, wherein R is hydrogen or lower alkyl, is reduced, utilizing, for example, lithium aluminum hydride, sodium dihydrobismethoxyethoxyaluminate or the like, and the resulting product is subsequently hydrolyzed to yield 6-chloro-3,4-dihydro-2-(2-hydroxymethylethyl)carbazole, that is, the compound of formula VI.

The obtained 6-chloro-3,4-dihydro-2-(2-hydroxymethylethyl)carbazole can be converted to an aromatized alcohol of the formula

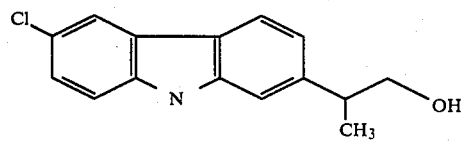

VII which is a known compound, utilizing the procedure described for the aromatization of the compounds of formula V hereinbefore.

The intermediate 6-chloro-1,2,3,4-tetrahydrocarbazole-2-one, that is, the compound of formula I, can be prepared by reacting p-chlorophenylhydrazine with dihydroresorcinol to yield a compound of the formula

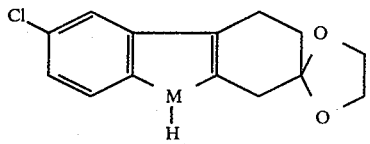

III which is then deketalized to a compound of formula I utilizing known procedures. The reaction conditions are further described by R. F. Borch and R. G. Newell in J. Org. Chem., 38, 2729 (1973).

The compound of formula V, when R is hydrogen, forms salts with pharmaceutically acceptable bases. Exemplary of such bases are alkali metal hydroxides, such as sodium hydroxide, potassium hydroxide, and the like; alkaline earth hydroxides, such as calcium hydroxide, barium hydroxide and the like; sodium alkoxides, such as sodium etholate, potassium etholate and the like; organic bases such as piperidine, diethanolamine, N-methylglucamine, and the like.

The compounds of formula II are known compounds which are useful in anti-inflammatory, analgesic and anti-rheumatic agents.

The compounds of formulas V and VI, including the salts of the compound of formula V when R is hydrogen, possess anti-inflammatory and anti-rheumatic properties. The compounds of formulas V and VI also exhibit a significantly low incidence of ulcerogenic activity, which renders them highly desirable as anti-inflammatory and anti-rheumatic agents. Their pharmacologically useful activities are demonstrated in warm-blooded animals using standard procedures.

For example, the anti-inflammatory activity is demonstrated in Albino rats of Hart Strain, weighing 125–155 gms. The test animals are given 10 mls. of vehicle[1], which contains the test compound per kg. of body weight. The animals are treated daily for five consecutive days. Three hours after the first treatment, 0.05 ml. of an 0.5% suspension of heat killed dessiccated Mycobacterium butyricum in U.S.P. olive oil, which has been steam sterilized for 30 minutes, is injected into the right hind foot of each rat. The paw volume is measured immediately after the injection of the adjuvant and again 96 hours later. The difference is recorded as volume of edema. The paw volume is measured by immersion of the paw into a column of mercury to an ink mark exactly at the level of lateral malleolus. Percent inhibition is calculated by dividing the average control edema minus the average treatment edema by the average control edema times 100. The percent inhibition is plotted against dose on semilogarithmic probability paper and the dose required to produce a 30% reduction in edema is estimated therefrom and is expressed as $ED_{30}$.

[1]Hilgar, A. G. and Hummel, D. J.: Endocrine Bioassay Data, No. 1, p. 15, August 1964 (Cancer Chemotherapy National Service Center, N.I.H.)

When 6-chloro-3,4-dihydro-2-(2-hydroxy-methylethyl)carbazole and 3,4-dihydro-6-chloro-α-methylcarbazole-2-acetic acid are utilized as test substances at a dosage of 0.03 mg. p.o., an anti-inflammatory activity is observed, that is, the edemas are reduced, respectively, by 11.7% and 37.6%.

The compounds of formulas V and VI have effects qualitatively similar to those of phenylbutazone and indomethacin, known for their therapeutic uses and properties. Thus, the end products of this invention demonstrate a pattern of activity associated with anti-inflammatory agents of known efficacy and safety.

The compounds of formulas V and VI can be incorporated into standard pharmaceutical dosage forms, for example, they are useful for oral or parenteral application with the usual pharmaceutical adjuvant material, for example, organic or inorganic inert carrier materials such as water, gelatin, lactose, starch, magnesium stearate, talc, vegetable oils, gums, polyalkyleneglycols, and the like. The pharmaceutical preparations can be employed in a solid form, for example, as tablets, troches, suppositories, capsules, or in liquid form, for example, as solutions, suspensions or emulsions. Pharmaceutical adjuvant materials can be added and include preservatives, stabilizers, wetting or emulsifying agents, salts to change the osmotic pressure or to act as buffers. The pharmaceutical preparations can also contain other therapeutically active substances.

The Examples which follow further illustrate the invention. All temperatures are in degrees Centigrade, unless otherwise mentioned.

EXAMPLE 1

Preparation of 6-chloro-2,2-ethylenedioxy-1,2,3,4-tetrahydrocarbazole

To a suspension of 17.90 g. of p-chlorophenylhydrazine hydrochloride in 400 ml. of toluene was added 13.4 g. of dihydroresorcinol. The mixture was heated at reflux, with azeotropic removal of water under nitrogen for 10 minutes. The suspension was cooled slightly, treated with 50 ml. of ethylene glycol and 2.28 g. of p-toluenesulfonic acid monohydrate, and heated for an additional 4.0 hours. The mixture was cooled, treated with water, and filtered. The organic layer was washed with water, saturated sodium bicarbonate solution and brine and dried over sodium sulfate. The material obtained upon solvent removal was crystallized from ether/30°-60° petroleum ether to give 14.70 g. of 6-chloro-2,2-ethylenedioxy-1,2,3,4-tetrahydrocarbazole, as a tan powder, mp 128°-238°.

EXAMPLE 2

Preparation of 6-chloro-1,2,3,4-tetrahydrocarbazole-2-one

A suspension of 6-chloro-2,2-ethylenedioxy-1,2,3,4-tetrahydrocarbazole in 200 ml. of 1:1 acetic acid/water was heated at reflux under nitrogen for 1.5 hours. The mixture was filtered hot and the filtrate was cooled in an ice bath and again filtered. Crystallization of the solid from methylene chloride/30°-60° petroleum ether gave 5.74 g. (26% yield) of 6-chloro-1,2,3,4-tetrahydrocarbazole-2-one as a flocculent solid, mp 194°-196°.

EXAMPLE 3

Preparation of racemic 6-chloro-3,4-dihydrocarbazole-2-α-methylacetic acid ethyl ester 6.12 g. (50% in mineral oil) of sodium hydride were suspended in 125 ml. of benzene. A solution of 30.9 g. of triethyl α-methylphosphonoacetate in 125 ml. of benzene was added over 1.0 hour to give a grey-green solution. 6.35 g. of 6-chloro-1,2,3,4-tetrahydrocarbazole-2-one was added in one portion and the mixture was heated at 40°-45° for 1.5 hours. The reaction mixture was washed with 0.25 N hydrochloric acid, water and brine and dried over sodium sulfate. The material obtained upon solvent removal was chromatographed on silica gel with 8:2 benzene/ethyl acetate and crystallized from ether/30°-60° petroleum ether to give 6.35 g. of racemic 6-chloro-3,4-dihydrocarbazole-2-α-methylacetic acid ethyl ester, mp 101°-102°.

EXAMPLE 4

Preparation of racemic 6-chloro-α-methylcarbazole-2-acetic acid ethyl ester

A mixture of 1.52 g. of racemic 6-chloro-3,4-dihydrocarbazole-2-α-methylacetic acid ethyl ester and 1.84 g. of chloranil in 50 ml. of toluene was heated at reflux under nitrogen for 4.0 hours. The suspension was cooled, filtered, washed with 0.5 N sodium hydroxide, water and brine, dried over sodium sulfate and stripped of solvent. The residual semi-solid was chromatographed on silica gel with 9:1 benzene/ethyl acetate and crystallized from benzene/hexane to give 1.38 g. of racemic 6-chloro-α-methylcarbazole-2-acetic acid ethyl ester, mp 113°-114°.

EXAMPLE 5

Preparation of 6-chloro-3,4-dihydrocarbazole-2-α-methylacetic acid

To a solution of 3.03 g. of 6-chloro-3,4-dihydrocarbazole-2-α-methylacetic acid ethyl ester in 50 ml. of ethanol was added 50 ml. of 2 N sodium hydroxide solution. The mixture was stirred 18 hours at 20° and acidified with 2 N hydrochloric acid. The resultant product was collected by filtration and crystallized from ether and 30°-60° petroleum ether to give 2.55 g. of 6-chloro-3,4-dihydrocarbazole-2-α-methylacetic acid as a white solid, mp 140°-141° (dec.).

EXAMPLE 6

Preparation of 6-chloro-3,4-dihydrocarbazole-2-(2-hydroxy-1-methylethyl)carbazole To an ice cold solution of 303 mg. of 6-chloro-3,4-dihydrocarbazole-2-α-methylacetic acid ethyl ester in 10 ml. of tetrahydrofuran was added, over 15 minutes, 2 ml. of a 70% solution of sodium dihydro-bis(2-methoxyethoxy)aluminate in benzene. The mixture was stirred at 3° for 90 minutes and treated, in order, with 5 ml. of methanol, 15 ml. of water and 50 ml. of ether. The organic phase was washed with 0.5 N hydrochloric acid, water and brine, dried over sodium sulfate and stripped of solvent to give a pale yellow oil. Two crystallizations of this material from ether and 30°-60° petroleum ether gave 153 mg. of 6-chloro-3,4-dihydrocarbazole-2-(2-hydroxy-1-methylethyl)carbazole, as a slightly off-white solid, mp 126°-127°.

EXAMPLE 7

| Suppository Formulation | |
|---|---|
| | Per 1.3 Gm. Suppository |
| 6-Chloro-3,4-dihydrocarbazole-α-methyl-2-acetic acid | 0.025 gm. |
| Wecobee M* | 1.230 gm. |
| Carnauba Wax | 0.045 gm. |

*E.F. Drew Company, 522 Fifth Avenue, New York, New York

Procedure:

1. The Wecobee M and the carnauba wax were melted in a suitable size glass-lined container (stainless steel may also be used), mixed well and cooled to 45° C.
2. 6-Chloro-3,4-dihydrocarbazole-α-methyl-2-acetic acid, which had been reduced to a fine powder with no lumps, was added and stirred until completely and uniformly dispersed.
3. The mixture was poured into suppository molds to yield suppositories having an individual weight of 1.3 gms.
4. The suppositories were cooled and removed from molds. They were individually wrapped in wax paper for packaging. (Foil may also be used.)

EXAMPLE 8

| Tablet Formulation | |
|---|---|
| | Per Tablet |
| 6-Chloro-3,4-dihydrocarbazole-α-methyl-2-acetic acid | 25.00 mg. |
| Lactose, U.S.P. | 64.50 mg. |
| Corn Starch | 10.00 mg. |
| Magnesium Stearate | 0.50 mg. |

Procedure:
1. 6-Chloro-3,4-dihydrocarbazole-α-methyl-2-acetic acid was mixed with the lactose, corn starch and magnesium stearate in a suitable mixer.
2. The mixture was further blended by passing through a Fitzpatrick Comminuting Machine fitted with a No. 1A screen with knives forward.
3. The mixed powders were slugged on a tablet compressing machine.
4. The slugs were comminuted to a suitable mesh size (No. 16 screen) and mixed well.
5. The tablets were compressed at a tablet weight of 100 mg. using tablet punches having a diameter of approximately one-fourth inch. (Tablets may be either flat or biconvex and may be scored if desired.)

EXAMPLE 9

| Capsule Formulation | |
|---|---|
| | Per Capsule |
| 6-Chloro-3,4-dihydrocarbazole-α-methyl-2-acetic acid | 50 mg. |
| Lactose, U.S.P. | 124 mg. |
| Corn Starch, U.S.P. | 30 mg. |
| Talc, U.S.P. | 5 mg. |
| Total Weight | 210 mg. |

Procedure:
1. 6-Chloro-3,4-dihydrocarbazole-α-methyl-2-acetic acid was mixed with lactose and corn starch in a suitable mixer.
2. The mixture was further blended by passing through a Fitzpatrick Comminuting Machine with a No. 1A screen with knives forward.
3. The blended powder was returned to the mixer, the talc added and blended thoroughly.
4. The mixture was filled into No. 4 hard shell gelatin capsules on a Parke Davis capsulating machine.

EXAMPLE 10

| Parenteral Formulation | |
|---|---|
| Each 1 cc. ampul contains: | Per cc: |
| 6-Chloro-3,4-dihydrocarbazole-α-methyl-2-acetic acid | 10.2 mg. (2% excess) |
| Methyl Paraben, U.S.P. | 1.8 mg. |
| Propyl Paraben, U.S.P. | 0.2 mg. |
| Sodium Hydroxide, U.S.P. q.s. ph | 9.0 |
| Water for Injection, U.S.P. q.s. ad | 1 cc. |

Procedure (For 10,000 cc.):
1. In a clean glass or glass-lined vessel, 8,000 cc. of Water for Injection were heated to 90° C. It was then cooled to 50°–60° C. and 18 gms. of methyl paraben and 2 gms. of propyl paraben were added and dissolved with stirring. The solution was then allowed to cool to room temperature.
2. The 102.0 gms. of 6-chloro-3,4-dihydrocarbazole-α-methyl-2-acetic acid were added under an atmosphere of nitrogen and stirred until completely dispersed.
3. The sodium hydroxide was added as a 10% solution until the pH was adjusted to 9.0 plus or minus 0.2, and the drug was completely dissolved.
4. Sufficient water for injection was then added to make a total volume of 10,000 cc.
5. This solution was then filtered through an 02 Selas candle, filled into suitable size ampuls, gassed with nitrogen, and sealed. It was autoclaved at 10 lbs. PSI for 30 minutes.

We claim:
1. A process for preparing 6-chloro-α-methylcarbazole-2-acetic acid and esters thereof which comprises the steps of (a) reacting 6-chloro-1,2,3,4-tetrahydrocarbazole-2-one with tri-lower alkyl-α-methylphosphonoacetate in the presence of a strong base, and (b) aromatizing the reaction product of step (a), prior to or after saponification, to yield 6-chloro-α-methylcarbazole-2-acetic acid or ester.

* * * * *